United States Patent
Stierli et al.

(10) Patent No.: US 9,073,839 B2
(45) Date of Patent: Jul. 7, 2015

(54) PROCESS FOR THE PREPARATION OF SUBSTITUTED PHENYLPROPANONES

(75) Inventors: Daniel Stierli, Stein (CH); Harald Walter, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/379,013

(22) PCT Filed: Feb. 28, 2012

(86) PCT No.: PCT/EP2012/053371
§ 371 (c)(1), (2), (4) Date: Aug. 15, 2014

(87) PCT Pub. No.: WO2013/127441
PCT Pub. Date: Sep. 6, 2013

(65) Prior Publication Data
US 2015/0031919 A1  Jan. 29, 2015

(51) Int. Cl.
*C07C 45/45* (2006.01)
*C07C 45/51* (2006.01)

(52) U.S. Cl.
CPC ............. *C07C 45/455* (2013.01); *C07C 45/516* (2013.01)

(58) Field of Classification Search
CPC .............................. C07C 45/45; C07C 45/455
USPC ...................................................... 568/319
See application file for complete search history.

(56) References Cited

U.S. PATENT DOCUMENTS

2008/0221198 A1   9/2008   Zhao et al.

FOREIGN PATENT DOCUMENTS

| WO | 0034229 | 6/2000 |
|---|---|---|
| WO | 2010063700 | 6/2010 |

OTHER PUBLICATIONS

Li Lia et al., Facile synthesis of 1-Aryl-s-propanones from Aromatic Amine, Synthetic Communications, 2007; 37(6): 985-991.
International Search Report dated Oct. 5, 2012 for International Patent Application No. PCT/EP2012/053371.

*Primary Examiner* — Sikarl Witherspoon
(74) *Attorney, Agent, or Firm* — R. Kody Jones

(57) ABSTRACT

The invention relates to a process for the preparation of a compound of formula (I) wherein the substituents are defined as in claim 1, which process comprises adding a compound of formula (II), wherein $R_1$, $R_2$ and $R_3$ have the meanings as described under formula (I), in the presence of an inert organic solvent, to a mixture comprising an organic nitrite of formula (III) R4-O—N=O, wherein $R_4$ is $C_1$-$C_8$alkyl, a compound of formula (IV), and an inert organic solvent.

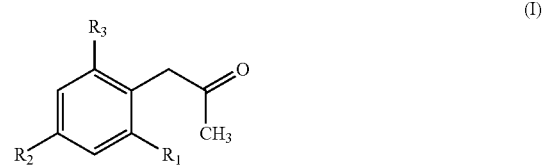

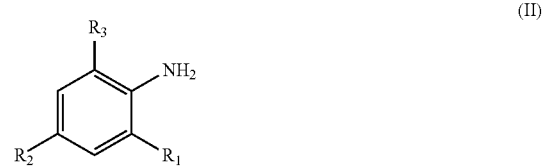

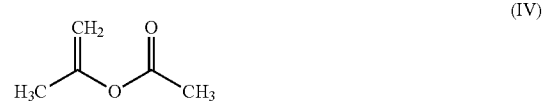

3 Claims, No Drawings

PROCESS FOR THE PREPARATION OF SUBSTITUTED PHENYLPROPANONES

RELATED APPLICATION INFORMATION

This application is a 371 of International Application No. PCT/EP2012/053371, filed Feb. 28, 2012, the contents of which are incorporated herein by reference herein.

The present invention relates to a process for the preparation of propane-2-one-substituted phenyls, in particular to the preparation of 1-(2,4,6-trihalo-phenyl)-propan-2-ones.

Propane-2-one-substituted phenyls are valuable intermediates for the preparation of fungicidally active pyrazole carboxamides, as described for example in WO 2010/063700.

It is known from scheme 3 on page 11 of WO 2010/063700 to prepare propane-2-one-substituted phenyls by a) reducing a compound of formula XIX to a compound of formula XX,

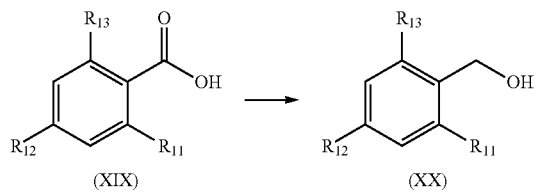

wherein $R_{11}$ is hydrogen, halogen or $C_1$-$C_6$alkyl;

$R_{12}$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C(C_1$-$C_4$alkyl)=NO—$C_1$-$C_4$alkyl, $C_1$-$C_6$haloalkyl, $C_1$-$C_6$haloalkoxy, $C_2$-$C_6$haloalkenyl, or $C_2$-$C_6$haloalkenyloxy; and $R_{13}$ is hydrogen, halogen or $C_1$-$C_6$alkyl;

b) reacting the compound of formula XX to an activated benzylic derivative of formula XXI,

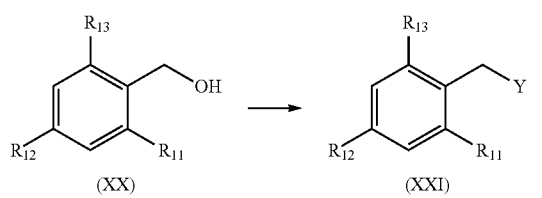

wherein Y represents a leaving group, such as halogen, mesylate or tosylate, c) reacting the compound of formula XXI to the nitril derivative of formula XXII

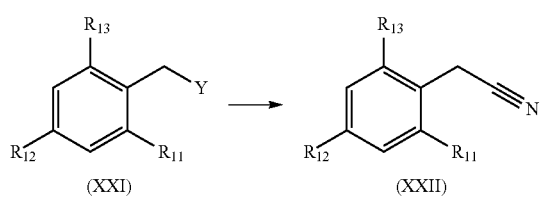

and d) reacting the compound of formula XXII with a Grignard reagent of the formula $R_5$—MgBr, wherein $R_5$ is for example methyl, to the propane-2-one-substituted phenyl of formula Xa (wherein $R_5$ is methyl).

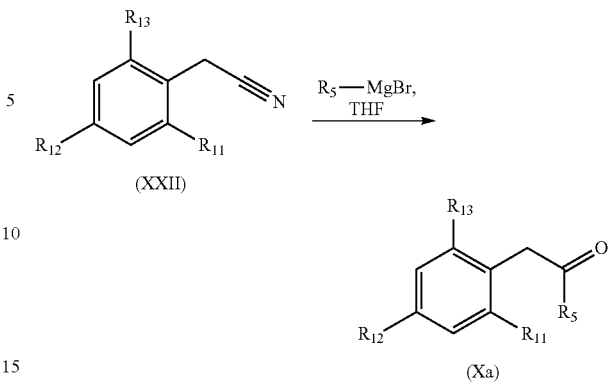

A disadvantage of this prior art process is the high production costs caused by the significant number of reaction steps which makes this process uneconomical and especially unsuitable for a large-scale production.

WO 00/34229 describes a process for the preparation of a ketone of formula V

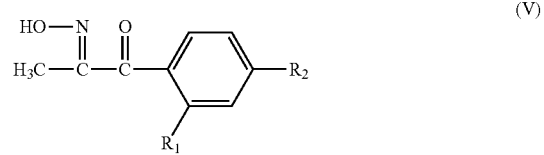

by diazotizing an aniline of formula VI

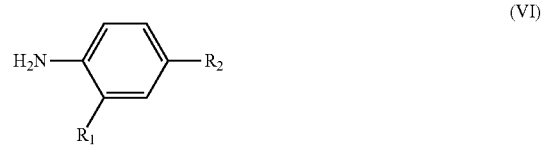

and reacting the resulting diazonium salt with isopropenylacetate of formula X
and reacting the resulting ketone of formula XI

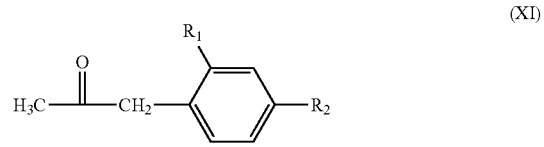

with an organic nitrite in the presence of hydrogen chloride.

A disadvantage of this process is the accumulation of the very reactive diazonium salt in the reaction mixture. Diazonium salts in general are sensitive to physical agents such as heat, light, shock, static electricity and dehydration that can lead to rapid, uncontrollable decompositions and explosions.

A further disadvantage is that 2 different equipments are needed to perform the reactions.

The aim of the present invention is therefore to provide a novel process for the production of propane-2-one-substituted phenyls that avoids the disadvantages of the known process and makes it possible to prepare propane-2-one-substituted phenyls in high yields and good quality in an economically advantageous way with less reaction steps.

Thus, according to the present invention, there is provided a process for the preparation of the compound of formula I

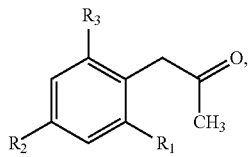
(I)

wherein
R₁ is hydrogen, halogen or $C_1$-$C_6$alkyl;
R₂ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C(C_1$-$C_4$alkyl)=NO—$C_1$-$C_4$alkyl, $C_1$-$C_6$haloalkyl,
$C_1$-$C_6$haloalkoxy, $C_2$-$C_6$haloalkenyl or $C_2$-$C_6$haloalkenyloxy; and
R₃ is hydrogen, halogen or $C_1$-$C_6$alkyl;
which process comprises
adding a compound of formula II

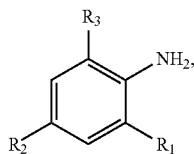
(II)

wherein R₁, R₂ and R₃ have the meanings as described under formula I, in the presence of an inert organic solvent, to a mixture comprising an organic nitrite of formula III $$R_4\text{—O—N=O} \quad \text{(III),}$$

wherein R₄ is $C_1$-$C_8$alkyl, a compound of formula IV

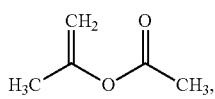
(IV)

and an inert organic solvent.

The process according to the invention uses easily accessible and nontoxic starting material, without the need of isolation or accumulation of diazonium salt and is therefore especially suitable for the large-scale preparation of a compound of formula I.

The process according to the invention is especially suitable for the production of compounds of formula I, wherein at least one of R₁, R₂ and R₃ is different from hydrogen. The process according to the invention is especially suitable for the preparation of compounds of formula I, wherein at least one of R₁, R₂ and R₃ is halogen.

Further compounds of formula I can be advantageously prepared, wherein R₁, R₂ and R₃ are all halogen, especially chloro. Compounds of formula I which can be advantageously prepared according to the process of this invention are described in Table 1.

TABLE 1

Preferred compounds of formula I (I)

| No. | R₁ | R₂ | R₃ |
|---|---|---|---|
| 1.01 | Cl | Cl | Cl |
| 1.02 | Cl | H | Cl |
| 1.03 | Cl | Cl | H |
| 1.04 | Cl | Br | Cl |
| 1.05 | Br | Br | Br |
| 1.06 | H | Cl | H |
| 1.07 | H | Br | H |
| 1.08 | H | CF₃ | H |

The compound of formula V can be prepared preferably by a one pot reaction adding the aniline of formula II to a mixture of isoprenylacetate of formula IV, an organic nitrite of formula III and a solvent. In preferred compounds of formula III, R₄ is $C_4$-$C_7$alkyl. A preferred nitrite is tert-butyl nitrite.

The mixture of isoprenylacetate of formula IV, an organic nitrite of formula III and a solvent can additionally contain a copper compound which can be advantageous to increase yield and/or quality of the product. Preferred copper compounds are CuO, $CuCl_2$ or $CuSO_4$. The amount of the copper compounds is preferably is 1-20 mol % in the relation to the aniline of formula II. Advantageous for the reaction is a temperature of −10° C. to 50° C. No isolation or accumulation of the diazonium salt is required for this process step. Preferably, the same solvent is used for the aniline of formula II and the mixture of isoprenylacetate of formula IV, and the organic nitrite of formula III. Suitable inert organic solvents are for example ketones, for example acetone, methylethylketone (MEK) or nitriles, for example acetonitrile. Preferred solvents are acetone and acetonitrile.

The compounds of formula II and III are either known or can be prepared according to methods well known in the art. Some compounds of formula II are commercially available, e.g. the compound of formula II, wherein R₁, R₂ and R₃ is chloro. Isoprenylacetate of formula IV is commercially available.

PREPARATORY EXAMPLES

Example P1

Preparation of 1-(2,4,6-trichloro-phenyl)-propan-2-one (Compound CAS1228284-86-3)

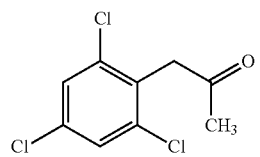

In a 1.5 l sulfonation flask equipped with mechanical stirring, cooling funnel, dropping funnel and thermometer under nitrogen at ambient temperature filled with acetone (240 ml), were added isopropenyl acetate (66 ml, 0.60 mol), tert-butyl nitrite (40 ml, 0.30 mol) and cupric sulfate pentahydrate (2.5 g, 0.001 mol). The resulting light green-blue suspension is stirred for 15 min at ambient temperature. A solution of 2,4,6-trichloroaniline (40 g, 0.20 mol), dissolved in acetone (320 ml) was added dropwise over a period of 2 hours. During the addition, bubbling observed, temperature rose to 30° C. and the mixture turned green. 1 Hour after the addition, an amber solution was obtained. The mixture was stirred for 6 hours. Completion of the reaction was confirmed by GC-MS. The crude mixture was concentrated under reduce pressure to remove most of the acetone and the residue was dissolved in ethyl acetate (300 ml) and wash with 1M hydrochloric acid (2×300 ml), water (2×300 ml) potassium carbonate solution (300 ml) followed by water (300 ml). Combined basic aqueous were re-extracted with of ethyl acetate (150 ml). Combined organics were dried over sodium sulfate, and the organics were concentrated under reduced pressure to give crude 1-(2,4,6-trichloro-phenyl)-propan-2-one (53 g) as a dark brown oil. The crude was dissolved again in ethyl acetate (200 ml) and washed with 1M sodium hydroxide (300 ml) 1M hydrochloric acid (100 ml) and water (200 ml). The organic layers were dried and evaporated to give crude 1-(2,4,6-trichloro-phenyl)-propan-2-one 49 g dark brown oil which crystallized.

$^1$H NMR (400 MHz, CDCl$_3$): δ 2.26 (s, 3H, CH$_3$), 4.05 (s, 2H, CH$_2$), 7.34 (s, 2H, Ar—H)

Example P2

Preparation of 1-(4-bromo-2,6-dichloro-phenyl)-propan-2-one

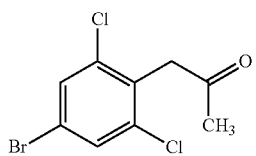

In a 50 ml three-neck flask equipped with mechanical stirring, cooling funnel, dropping funnel and thermometer under nitrogen at ambient temperature filled with acetonitrile (10 ml), were added cuprous oxide (1.5 g, 0.018 mol), isopropenyl acetate (13.6 ml, 0.125 mol) and tert-butyl nitrite (1.7 ml, 0.0125 mol). The resulting red suspension is stirred for 15 min at ambient temperature. A solution of 4-bromo-2,6-dichloroaniline (2.0 g, 0.0083 mol), dissolved in acetonitrile (15 ml) was added dropwise over a period of 20 minutes. During the addition, bubbling was observed. The mixture was stirred at 40° C. for 20 hours. The red crude mixture was passed through celite to remove solid particles and concentrated under reduce pressure to give a brown solid. The residue was dissolved in dichloromethane (120 ml) and washed with water (2×50 ml) and brine (40 ml). Organics were dried over sodium sulfate and concentrated under reduced pressure to give crude 1-(4-bromo-2,6-dichloro-phenyl)-propan-2-one (2.3 g) as a dark brown oil.

$^1$H NMR (400 MHz, CDCl$_3$): δ 2.25 (s, 3H, CH$_3$), 4.06 (s, 2H, CH$_2$), 7.50 (s, 2H, Ar—H)

Example P3

Preparation of 1-(2,4,6-trichloro-phenyl)-propan-2-one

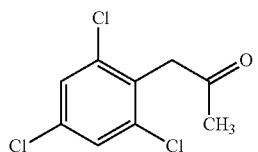

A mixture of isopropenyl acetate (12.2 g, 122 mmol), 2,4,6-trichloroaniline (16.0 g, 81.4 mmol), potassium carbonate (100 mg, 0.7 mmol), and acetone (100 g) was cooled to 10° C. tert-Butyl nitrite (90%, 10 g, 87.3 mmol) was dosed over 30 minutes. The reaction was stirred for further 90 minutes, and it was concentrated to a black oil. The residue was triturated with water, and the pH was adjusted to 10.5 with sodium hydroxide solution. The precipitate was filtered and recrystallized from methanol-water 1:1. The solid was filtered, washed with methanol-water 1:1, and dried. The product was obtained as dark-brown crystalline material (15.9 g, 70.7% purity, 47.3 mmol, 58% yield). Further purification was achieved by recrystallization from hexanes. 1H NMR (400 MHz, CDCl$_3$): δ 2.23 (s, 3H, CH$_3$), 4.02 (s, 2H, CH$_2$), 7.31 (s, 2H, CH).

What is claimed is:

1. A process for the preparation of the compound of formula I

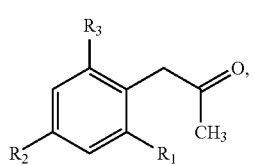

(I)

wherein

R$_1$ R$_2$ and R$_3$ are halogen which process comprises adding a compound of formula II

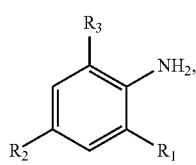

(II)

wherein R$_1$, R$_2$ and R$_3$ have the meanings as described under formula I, in the presence of an inert organic solvent to a mixture comprising an organic nitrite of formula III

R$_4$—O—N═O (III), wherein $R_4$ is $C_1$-$C_8$alkyl, a compound of formula IV
(IV)
and an inert organic solvent.
2. A process according to claim 1 for the preparation of a compound of formula I, wherein $R_1$, $R_2$ and $R_3$ are chloro.
3. A process according to claim 1 for the preparation of a compound of formula I, wherein $R_4$ is $C_4$-$C_7$alkyl.
\* \* \* \* \*